United States Patent [19]

Williams

[11] Patent Number: 4,662,877

[45] Date of Patent: May 5, 1987

[54] SHAPED DISPOSAL DIAPER

[75] Inventor: Frank C. Williams, New South Wales, Australia

[73] Assignee: Johnson & Johnson, New Brunswick, N.J.

[21] Appl. No.: 760,695

[22] Filed: Jul. 30, 1985

[30] Foreign Application Priority Data

Aug. 2, 1984 [AU] Australia .................................. 6359

[51] Int. Cl.$^4$ ............................................ A61F 13/16
[52] U.S. Cl. ................................................ 604/385 A
[58] Field of Search .................. 604/385.1, 385.2, 378, 604/358

[56] References Cited

U.S. PATENT DOCUMENTS

| 4,285,342 | 8/1981 | Mesek ............................ 604/385.2 |
| 4,324,245 | 4/1982 | Mesek et al. ..................... 604/385.2 |
| 4,430,086 | 2/1984 | Repke ............................ 604/385.2 |

*Primary Examiner*—John D. Yasko
*Attorney, Agent, or Firm*—Martha A. Michaels; Lawrence D. Schuler

[57] ABSTRACT

A disposable diaper has a moisture impermeable backing sheet, a fibrous absorbent batt and a flexible hydrophobic facing sheet overlying the batt, the components being secured together to form a sandwich structure; the facing sheet has an aperture in the central crotch region of the diaper with zones of elastication in the facing sheet tending to apply tensioning forces to the facing sheet for urging the facing sheet (at least in the regions adjacent the aperture) away from the underlying batt structure. With advantage the facing sheet is a breathable web of bonded fibres highly resistant to permeation of moisture. It is preferred that the absorbent batt structure comprises a wood-pulp batt and a non-woven sheet of moisture permeable material overlying the absorbent batt.

14 Claims, 4 Drawing Figures

SHAPED DISPOSAL DIAPER

The present invention relates to disposable diapers.

Conventionally disposable diapers comprise a liquid impermeable plastic backing sheet, a wood-pulp absorbent batt and a moisture permeable facing sheet, the components being secured together by lines of adhesive with the backing and facing sheets usually directly adhesively interconnected around peripheral portions of the diaper. Some disposable diapers include elastic bands for providing a shaping and/or gathering effect for the diaper in the crotch region and facilitating the establishment of a fluid resistant seal around the infant's legs. Examples, of known diapers are found in Australian patent specification Nos. 526338 and 528786.

It would be desirable for a disposable diaper to be of a design which can be constructed very cheaply yet efficiently in a high speed manufacturing machine but also provide excellent performance in effectively containing and retaining liquid discharges despite normal bodily movements of an infant. When an infant voids, a considerable volume of liquid is released at a localised region of the crotch portion of the diaper and this release is relatively fast thereby imposing considerable demands upon the performance of the absorbent material which usually has a wicking effect to disperse the urine. Furthermore in the case of a male baby, it is possible for the discharge of urine to be directed upwardly away from the crotch region and effective containment can be a problem.

It is also desirable for a disposable diaper to be conformable to the shape of the baby so as to have a good appearance and provide a high degree of comfort even after a liquid discharge has taken place.

Thus, there are many challenging requirements for disposable diapers and conflicting requirements.

The present invention is directed to a new and useful alternative to previous proposals.

According to the present invention there is provided a disposable diaper comprising a moisture impermeable backing sheet, a fibrous absorbent batt structure, a flexible hydrophobic facing sheet overlying the absorbent batt, the components being secured together to form a sandwich structure, and an aperture being provided in said facing sheet in the central crotch region of the diaper with zones of elastication being provided in the facing sheet tending to apply tensioning forces to the facing sheet and urging the facing sheet at least in the regions adjacent said aperture away from the underlying batt structure.

In this specification, the term "hydrophobic facing sheet" means a sheet resistant to wicking of moisture along the sheet and resistant to transmitting moisture through the sheet. Preferably, the facing sheet has a high degree of hydrophobicity and may have with advantage a sink time of greater than 12 hours in a basket sink time test according to A.S.T.M. Test Part 32 D-1117/80 Part V.

Furthermore the facing sheet preferably is of a carded rayon or similar fibre web bonded with a hydrophobic resin, the sheet being breathable and relatively soft to the touch. Typically the sheet will be 24 g.s.m. with good structural integrity.

The material used for the flexible facing sheet preferably is highly resistant to the penetration of liquid but is breathable and capable of penetration by moisture vapour. Examples of materials which may be used comprise a moisture repellant non-woven fabric, a melt blown polypropylene sheet, or an apertured polyethelene film. Except for the limited regions of the absorbent batt structure aligned with the aperture in the crotch region, the flexible facing sheet can provide a relatively dry and comfortable material to engage with the baby's body and can significantly enhance the resistance to leakage particularly in the region of the inside of the thighs, as well as from the ends of the nappy.

Preferably, the invention is applied to a disposable diaper having bands of elastication provided along the opposite marginal portions of the crotch region of the diaper for providing a gathering effect and establishing a seal around the infant's legs, the zones of elastication and the facing sheet being spaced from said bands of elastic. However, for economy of manufacture, these bands of elastication could be omitted leaving the hydrophobic facing sheet to provide a "seal" around the infant's legs.

Advantageously, the batt is of rectangular shape located with a diaper having an hour-glass overall shape.

A preferred and important embodiment of the invention has the zones of elastication of the facing sheet in the form of strips of elastication extending substantially parallel to the longitudinal direction of the diaper.

However, other elastication arrangements could be provided if desired; for example longitudinally extending bands of elastic extending from the waist band region of the diaper towards the central aperture might be used to provide the tensioning effect.

Although the surface portion of the absorbent batt remote from the backing sheet could be a treated surface portion of wood-pulp fibres (which are preferably absorbent fibres) a non-woven sheet of material which is readily permeable to moisture may be used with advantage to overlie the absorbent batt.

Another additional inventive and advantageous feature which can be usefully employed in embodiments of the invention is the provision of means for securing the facing sheet to the underlying material in a region intermediate the respective longitudinal sides of the aperture and the adjacent edge of the crotch region. Preferably, this interconnection is established by a line of adhesive such as hot melt adhesive which in a preferred embodiment attaches the facing sheet to the underlying non-woven fabric moisture permeable sheet.

It may be advantageous to close adhesively the diaper structure at one or both the waist band regions by bands of adhesive extending transversely across the structure. The adhesive may be applied in a band to the moisture impermeable backing sheet.

Since at least in a preferred embodiment of the invention the absorbent batt structure in the crotch region forms a sump-like collection feature for waste, only very limited contact between the baby's skin and wet portions of the diaper should occur.

The invention can be applied with various shapes and configurations for the aperture in the facing sheet. For example an oval aperture offset towards the front region of the diaper may be convenient with, for example, a width of about 12 cm and a length of about 30 cm. Typically these zones elastication are provided by elastic members about 5 mm wide in the unstretch condition and adhesively secured in position with an elongation of about 120% when the diaper is stretched out to its maximum extent. It is to be understood that the configuration of the aperture may be varied according to other parameters such as the exact configuration of the elastication of the facing sheet.

Another additional inventive feature which may be employed is the provision of elongated bands of elastication extending transversely of the diaper for the purpose of tensioning the facing sheet. For example one or more bands may be provided to extend from a region adjacent the edge of the aperture to the adjacent edge of the crotch region of the diaper.

For illustrative purposes only an embodiment of the invention will now be described with reference to the accompanying drawings of which:

Figure 1:
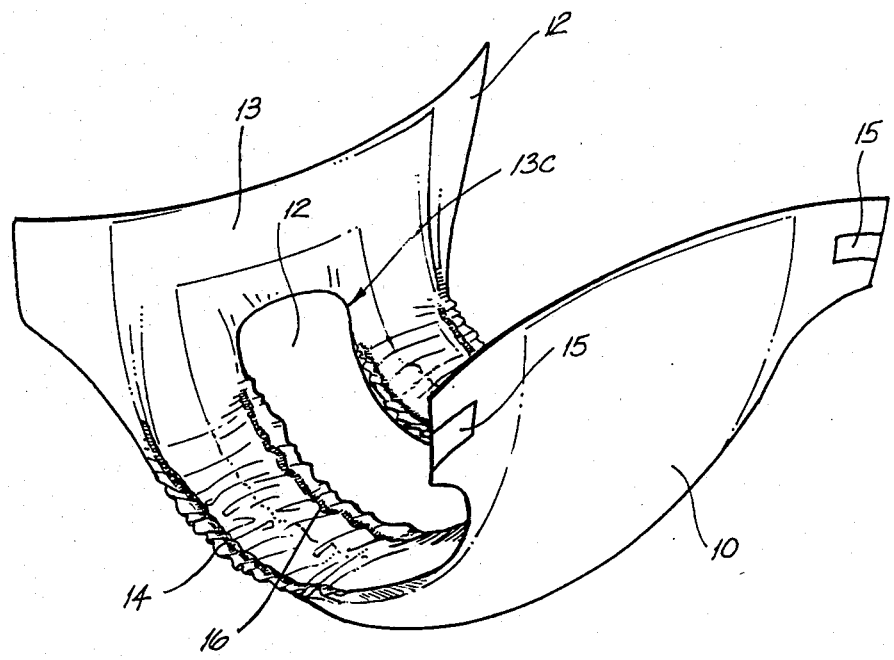
FIG. 1 is a sketch illustrating a diaper embodying the invention with the crotch region curved during commencement of application of the diaper to an infant.

The diaper shown in the drawings comprises a polyethelene plastic backing sheet 10 shaped to have cut-away intermediate side portions to provide a narrowed crotch region, a narrow rectangular absorbent batt 11, a moisture permeable non-woven fibrous batt cover sheet 12 and a hydrophobic substantially liquid impermeable non-woven fibrous facing sheet 13. The cover sheet 12 is of the same dimension as the backing sheet 10, these components being secured directly around the periphery of the diaper by parallel lines of hot melt adhesive extending in the longitudinal direction of the diaper but not shown in the drawing. These lines of hot melt adhesive also secure the absorbant batt 11 on the backing sheet 10.

The rectangular facing sheet 13 is adhesively attached to the cover sheet 12 by longitudinal lines 13A of hot-melt adhesive; the waist regions are adhesively closed by transverse bands 13B of hot melt adhesive. Each of the lines 13A and 13B of adhesive is applied to the cover sheet 12 and during assembly of the product the adhesive strikes through the cover sheet 12 and adhesively binds together the hacking sheet, cover sheet and facing sheet 13.

Adjacent each side of the crotch region, an elastic band 14 is provided for the purpose of gathering and shaping the diaper as well as providing for a leg seal effect around the infant's thighs. However, a reasonable degree of sealing may be established without such bands, the facing sheet 13 being gathered around the infant's thighs and resisting leakage. Adhesive tape tabs 15 are provided at the rear waistband corner regions for permitting attachment of the diaper to an infant.

Figure 2:
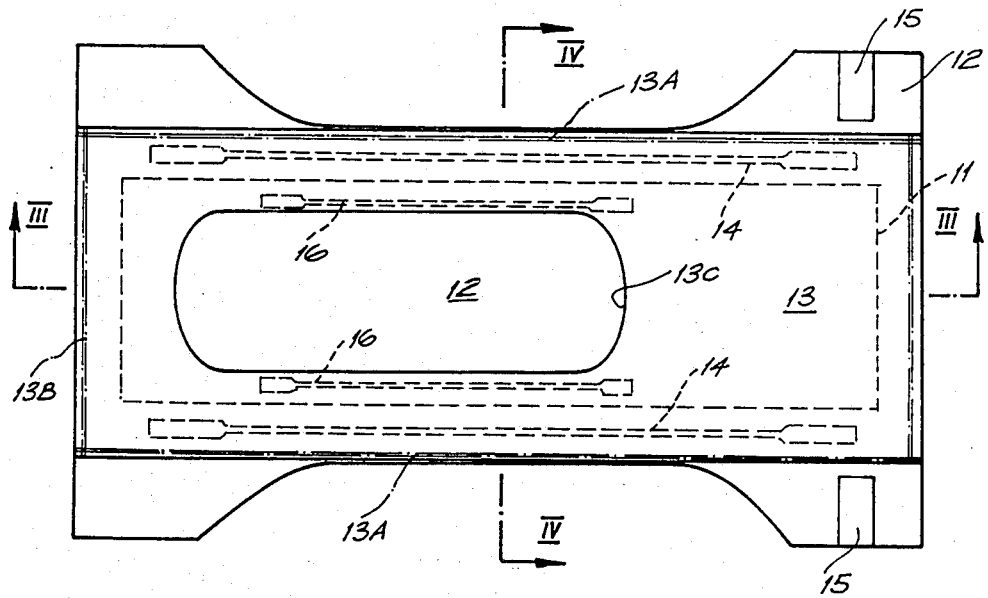
FIG. 2 is a plan view of the diaper of FIG. 1 when held in a flat and tensioned condition.
Figure 3:
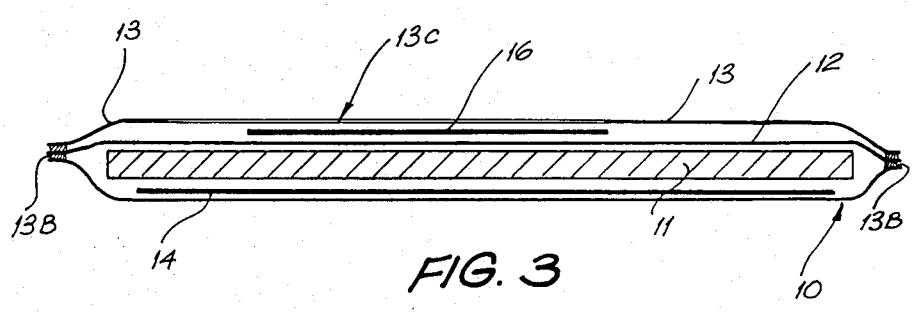
FIG. 3 is a schematic longitudinal cross sectional side elevation taken along the line III—III of FIG. 2.
Figure 4:
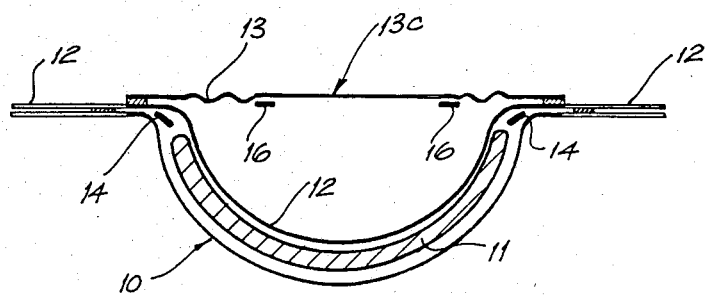
FIG. 4 is a transverse cross sectional elevation taken through the diaper along the line IV—IV of FIG. 2, but with the diaper relaxed ready for application to an infant; the parts are shown exaggerated for ease of depicting the structure.

As shown most clearly in FIG. 2, an oval shaped aperture 13C is provided in the facing sheet and is located offset towards the front of the diaper, the length of the aperture being chosen so that waste discharges will normally be directed through the aperture onto the centre of cover sheet 12 and through to the absorbent batt structure.

Elastication is provided for tensioning the facing sheet 13 in the crotch region of the diaper by longitudinal elastic bands 16. In use the facing sheet is urged to be spaced above the underlying absorbent batt.

The illustrated embodiment could include, as an optional feature, an adhesive interconnection between the facing sheet 13 and the underlying structure in the crotch region at a location between the edge of the crotch region and the edge of the aperture.

I claim:

1. A disposable diaper comprising a moisture impermeable backing sheet, a fibrous absorbent batt structure a flexible hydrophobic facing sheet (as herein defined) overlying the absorbent batt, the components being secured together to form a sandwich structure, and an aperture being provided in said facing sheet in the central crotch region of the diaper with zones of elastication being provided in the facing sheet tending to apply tensioning forces to the facing sheet and urging the facing sheet at least in the regions adjacent said aperture away from the underlying batt structure.

2. A disposable diaper as claimed in claim 1 wherein said facing sheet is of a material having a basket sink test time greater than 12 hours.

3. A disposable diaper as claimed in claim 2 and wherein the facing sheet comprises a breathable web of fibres bonded together by a hydrophobic resin and highly resistant to permeation of moisture.

4. A diaper as claimed in claim 1 and wherein said flexible facing sheet is selected from the group consisting of a moisture repellant non-woven fabric, a melt blown polyethylene sheet, an apertured polyethelene film and a breathable film incorporating microporous holes.

5. A diaper as claimed in claim 1, wherein the zones of elastication of the facing sheet are in the form of strips of elastication extending substantially parallel to the longitudinal direction of the diaper.

6. A diaper as claimed in claim 1, wherein the absorbant batt structure comprises a wood-pulp batt and a non-woven sheet of moisture permeable material overlying the absorbant batt.

7. A diaper as claimed in claim 1 and wherein the aperture in the facing sheet is elongated and is dimensioned to be approximately 12 cm wide and 30 cm long.

8. A diaper as claimed in claim 1, wherein the facing sheet is secured around its periphery by hot melt adhesive which secures the facing sheet directly or indirectly to the backing sheet.

9. A diaper as claimed in claim 1 and including transverse bands of adhesive at at least one of the waist band regions for adhesively closing the structure.

10. A diaper as claimed in claim 1 and having bands of elastic provided along the opposite marginal portions of the crotch region of the diaper for providing a gathering effect and establishing a seal around the infant's legs, the zones of elastication and the facing sheet being spaced from said bands of elastic.

11. A diaper as claimed in claim 10 and wherein the overall shape of the diaper is an hour-glass shape and the absorbant batt is a relatively narrow rectangular structure.

12. A disposable diaper comprising a moisture impermeable backing sheet, a fibrous absorbant batt structure, a flexible facing sheet overlying the absorbant batt, the components being secured together to form a sandwich structure, and an aperture being provided in said facing sheet in the central crotch region of the diaper with zones of elastication being provided in the facing sheet tending to apply tensioning forces to the facing sheet and urging the facing sheet at least in the regions adjacent said aperture away from the underlying batt structure; and wherein said facing sheet is a breathable web of fibres bonded together by a hydrophobic resin and highly resistant to permeation of moisture; said breathable web having a basket sink test time greater than 12 hours.

13. A disposable diaper as claimed in claim 12 wherein said flexible facing sheet is selected from the group consisting of a moisture repellent nonwoven fabric, a melt blown polypropylene sheet, an apertured polyethylene film and a breathable film incorporating microporous holes.

14. A disposable diaper as claimed in claim 12, wherein the zones of elastication of the facing sheet are in the form of strips of elastication extending substantially parallel to the longitudinal direction of the diaper and wherein the absorbant batt structure comprises a wood-pulp batt and a non-woven sheet of moisture permeable material overlying the absorbant batt.

* * * * *